(12) United States Patent
Inaniwa et al.

(10) Patent No.: US 10,792,516 B2
(45) Date of Patent: Oct. 6, 2020

(54) BEAM IRRADIATION TARGET CONFIRMATION DEVICE

(71) Applicant: NATIONAL INSTITUTES FOR QUANTUM AND RADIOLOGICAL SCIENCE AND TECHNOLOGY, Chiba-shi, Chiba (JP)

(72) Inventors: Taku Inaniwa, Chiba (JP); Takuji Furukawa, Chiba (JP); Koji Noda, Chiba (JP)

(73) Assignee: NATIONAL INSTITUTES FOR QUANTUM AND RADIOLOGICAL SCIENCE AND TECHNOLOGY, Chiba-shi (JP)

( * ) Notice: Subject to any disclaimer, the term of this patent is extended or adjusted under 35 U.S.C. 154(b) by 799 days.

(21) Appl. No.: 15/318,273

(22) PCT Filed: Jun. 10, 2015

(86) PCT No.: PCT/JP2015/002917
§ 371 (c)(1),
(2) Date: Dec. 12, 2016

(87) PCT Pub. No.: WO2015/190102
PCT Pub. Date: Dec. 17, 2015

(65) Prior Publication Data
US 2017/0113065 A1    Apr. 27, 2017

(30) Foreign Application Priority Data

Jun. 12, 2014  (JP) .................................. 2014-121174

(51) Int. Cl.
*A61N 5/10* (2006.01)
*A61B 6/00* (2006.01)
*A61B 6/03* (2006.01)

(52) U.S. Cl.
CPC ............ *A61N 5/1039* (2013.01); *A61B 6/032* (2013.01); *A61B 6/482* (2013.01); *A61B 6/5217* (2013.01);
(Continued)

(58) Field of Classification Search
CPC .... A61N 5/103; A61N 5/1039; A61N 5/1049; A61N 5/1065; A61N 5/1069;
(Continued)

(56) References Cited

U.S. PATENT DOCUMENTS

2004/0184583 A1* 9/2004 Nagamine ............ A61N 5/1049
378/209
2006/0241387 A1* 10/2006 Nagamine ................ A61B 6/04
600/415

(Continued)

FOREIGN PATENT DOCUMENTS

JP    2008-253758 A    10/2008
JP    2010-187991 A     9/2010
(Continued)

OTHER PUBLICATIONS

M. Yang, "Theoretical variance analysis of single- and dual-energy computed tomography methods for calculating proton stopping power ratios of biological tissues", 2010, Physics in Medicine & Biology, vol. 55, pp. 1343-1361 (Year: 2010).*

(Continued)

*Primary Examiner* — David J Makiya
*Assistant Examiner* — Soorena Kefayati
(74) *Attorney, Agent, or Firm* — Hamre, Schumann, Mueller & Larson, P.C.

(57) ABSTRACT

A beam irradiation target verification apparatus includes an X-ray switching emission process unit that causes a vertical X-ray emitting unit to emit at least two types of X-rays using an energy-level switching unit, a vertical X-ray detection (Continued)

unit that detects an X-ray emitted from the vertical X-ray emitting unit, a pre-therapy verification image generation process unit, a reference image acquisition unit that acquires a reference image obtained at a therapy planning stage, a comparison process unit. The pre-therapy verification image generation process unit to generate pre-therapy verification images based on detection information of at least two types of X-rays obtained by the vertical X-ray detection unit. The comparison process unit makes comparisons between the pre-therapy verification images and the reference image, and the result output unit outputs a comparison result obtained by the comparison process unit.

6 Claims, 3 Drawing Sheets (52) U.S. Cl.
CPC ............ *A61B 6/563* (2013.01); *A61N 5/1049* (2013.01); *A61N 5/1077* (2013.01); *A61B 6/5235* (2013.01); *A61N 5/103* (2013.01); *A61N 5/1065* (2013.01); *A61N 5/1069* (2013.01); *A61N 2005/1061* (2013.01); *A61N 2005/1087* (2013.01)

(58) Field of Classification Search
CPC .......... A61N 5/1077; A61N 2005/1061; A61N 5/1071; A61B 6/032; A61B 6/482; A61B 6/5217; A61B 6/5235; A61B 6/563
See application file for complete search history.

(56) References Cited

U.S. PATENT DOCUMENTS

| | | | | |
|---|---|---|---|---|
| 2007/0053492 A1* | 3/2007 | Kidani | ................ | A61B 6/463 378/65 |
| 2007/0110289 A1* | 5/2007 | Fu | ................ | A61B 6/4458 382/128 |
| 2008/0232664 A1* | 9/2008 | Nagamine | ................ | A61N 5/1048 382/131 |
| 2009/0003523 A1* | 1/2009 | Raanes | ................ | A61B 6/4458 378/65 |
| 2009/0274269 A1* | 11/2009 | Foland | ................ | A61N 5/1048 378/54 |
| 2010/0053208 A1* | 3/2010 | Menningen | ................ | G06F 19/321 345/619 |
| 2010/0232572 A1* | 9/2010 | Nord | ................ | A61N 5/103 378/65 |
| 2012/0008734 A1* | 1/2012 | Thomson | ................ | A61B 6/4085 378/4 |
| 2012/0280135 A1* | 11/2012 | Bal | ................ | A61B 6/5229 250/395 |
| 2013/0083895 A1* | 4/2013 | Umekawa | ................ | A61B 6/06 378/62 |
| 2013/0101082 A1* | 4/2013 | Jordan | ................ | A61N 5/1083 378/19 |
| 2013/0108014 A1* | 5/2013 | Tome | ................ | A61B 6/5217 378/21 |
| 2013/0163724 A1* | 6/2013 | Marash | ................ | A61N 5/1064 378/91 |
| 2013/0329856 A1* | 12/2013 | Kuwahara | ................ | A61B 6/032 378/62 |
| 2015/0006098 A1* | 1/2015 | Ju | ................ | A61N 5/10 702/84 |
| 2015/0030227 A1* | 1/2015 | Liang | ................ | A61B 6/032 382/131 |
| 2015/0161793 A1* | 6/2015 | Takahashi | ................ | A61N 5/1077 600/1 |
| 2015/0217137 A1* | 8/2015 | Takahashi | ................ | A61N 5/1039 600/1 |
| 2015/0272530 A1* | 10/2015 | Umekawa | ................ | A61N 5/1049 378/7 |
| 2016/0263399 A1* | 9/2016 | Matsuzaki | ................ | A61N 5/1049 |
| 2016/0287907 A1* | 10/2016 | Michaud | ................ | A61B 6/4258 |
| 2017/0112457 A1* | 4/2017 | Allinson | ................ | A61B 6/032 |
| 2017/0128029 A1* | 5/2017 | Penfold | ................ | G01N 23/04 |
| 2018/0263576 A1* | 9/2018 | Konno | ................ | A61B 6/4241 |
| 2019/0168028 A1* | 6/2019 | Dempsey | ................ | A61N 5/1071 |

FOREIGN PATENT DOCUMENTS

| | | | |
|---|---|---|---|
| JP | 2010187991 | * | 9/2010 |
| JP | 2011-234932 A | | 11/2011 |
| JP | 2013252420 A | | 12/2013 |

OTHER PUBLICATIONS

English machine translation of JP 2010187991 (Year: 2010).*
International Search Report and Written Opinion, International Patent Application No. PCT/JP2015/002917, dated Sep. 8, 2015 with English translation (12 pages).
Telsemeyer et al., "Quantitative carbon ion beam radiography and tomography with a flat-panel detector", Physics in Medicine and Biology (UK), IOP Publishing, Dec. 7, 2012, vol. 57, No. 23, pp. 7957-7971.
Alessandra Bolsi, "Daily Treatment Setup at PSI", Paul Scherrer Institut, Jan. 11, 2010 (11 pages).

* cited by examiner

BEAM IRRADIATION TARGET CONFIRMATION DEVICE

TECHNICAL FIELD

The present invention relates to a beam irradiation target verification apparatus, for example, for use prior to a particle beam therapy, to a beam irradiation target verification program, and to a stopping-power-ratio calculation program.

BACKGROUND ART

Conventionally, a particle beam therapy apparatus typically for proton beam therapy or carbon ion beam therapy has been utilized. Such a particle beam therapy apparatus exploits a feature that allows a particle beam to emit energy in a focused manner at a stopping location (i.e., at or near the end of travel), and is thus adjusted before use so that the particle beam will stop at the location of a tumor. Thus, the particle beam therapy apparatus achieves reduction in exposure of normal tissue, and at the same time, causes damage on the tumor in a focused manner. If the location, size, shape or the like of the tumor differs between those at the time of therapy planning and those at the time of therapy, the particle beam may stop at a location different from the location presumed at the time of therapy planning. Such difference may be caused by, for example, a change in location or a change in shape of a corresponding organ due to, for example, a difference in a posture or in an angle of the therapy patient relative to the particle beam therapy apparatus between those determined at the time of therapy planning and those at the time of therapy; by an increase or decrease in the body weight during the duration of therapy; or by shrinkage, enlargement or disappearance of the tumor. Stopping of the particle beam at a location different from the location of a therapy plan may result in an insufficient dose in the tumor, and in a harmful event such as exposure of a critical organ. Therefore, to figure out the beam range inside the body and a deviation from that of the therapy plan prior to routine therapy irradiation is important.

In this regard, a method has been proposed that performs computed tomography (CT) imaging prior to a therapy, and verifies the tumor location of the therapy patient using an image obtained by this CT imaging.

However, due to its structure, a CT imaging device cannot capture an image of the therapy patient lying in place on the therapy patient support table of a particle beam therapy apparatus. Accordingly, the therapy patient needs to move from the CT imaging device to the particle beam therapy apparatus. This results in an image generated by the CT imaging device that does not reflect any change in shape and change in location of the corresponding organ caused by the movement of the therapy patient. Thus, the conditions of the therapy patient may not necessarily be assured at the therapy location of the particle beam therapy apparatus.

Furthermore, performing CT imaging each time before a therapy causes an increase in the amount of exposure of the therapy patient during a therapy duration. Thus, a method that performs CT imaging each time before a therapy poses a problem in that a change in shape etc. of the organ caused by a movement of the therapy patient cannot be handled, as well as a problem in that the amount of exposure increases.

Carbon ion beam radiography has also been proposed that directly measures a two-dimensional image generated by integrally projecting stopping power ratios of the therapy patient along the beam axis direction (Non-Patent Literature 1). This carbon ion beam radiography measures a two-dimensional image by detecting the residual range of a carbon ion beam that has passed through the therapy patient.

However, a method using such carbon ion beam radiography needs acceleration of the carbon ion beam to an energy level sufficient for the carbon ion beam to pass through the therapy patient. Providing such acceleration requires a large-scale accelerator facility. Thus, a method using such carbon ion beam radiography poses a problem in not being usable in a typical particle beam therapy facility in which a large-scale accelerator facility cannot be installed.

In addition, a method using carbon ion beam radiography also poses a problem in involving an impractically long period of time and an unacceptable level of exposure in order to obtain an image with sufficiently high accuracy.

CITATION LIST

Non-Patent Literature

Non-Patent Literature 1: Julia Telsemeyer and two others, "Quantitative carbon ion beam radiography and tomography with a flat-panel detector," Physics in Medicine and Biology (UK), IOP Publishing, Dec. 7, 2012, vol. 57, no. 23, pp. 7957-7971.

SUMMARY OF THE INVENTION

Technical Problems

In view of the foregoing problems, it is an object of the present invention to provide a beam irradiation target verification apparatus, a beam irradiation target verification program, and a stopping-power-ratio calculation program, each capable of measuring internal conditions of a therapy patient determining necessity of changing a therapy plan, easily and at a relatively low exposure level.

Solution to Problems

The present invention is characterized as a beam irradiation target verification apparatus including an X-ray emitting unit configured to emit an X-ray, an energy-level switching unit configured to switch an energy level of the X-ray to be emitted, in the X-ray emitting unit, an X-ray switching emission process unit configured to cause the X-ray emitting unit to emit at least two types of X-rays using the energy-level switching unit, an X-ray detection unit configured to detect an X-ray emitted from the X-ray emitting unit, a pre-therapy verification image generation process unit configured to generate a pre-therapy verification image based on detection information of at least two types of X-rays obtained by the X-ray detection unit, a reference image acquisition unit configured to acquire a reference image obtained at a therapy planning stage, a comparison process unit configured to make a comparison between the pre-therapy verification image and the reference image, and a result output unit configured to output a comparison result obtained by the comparison process unit; and a beam irradiation target verification program or a stopping-power-ratio calculation program used therefor.

Advantageous Effects of Invention

According to the present invention, there are provided a beam irradiation target verification apparatus, a beam irradiation target verification program, and a stopping-power-ratio calculation program, each capable of measuring internal conditions of a therapy patient and determining necessity of changing a therapy plan, easily and at a relatively low exposure level.

DESCRIPTION OF EMBODIMENTS

An embodiment of the present invention will be described below with reference to the drawings.

Embodiment 1

Figure 1:
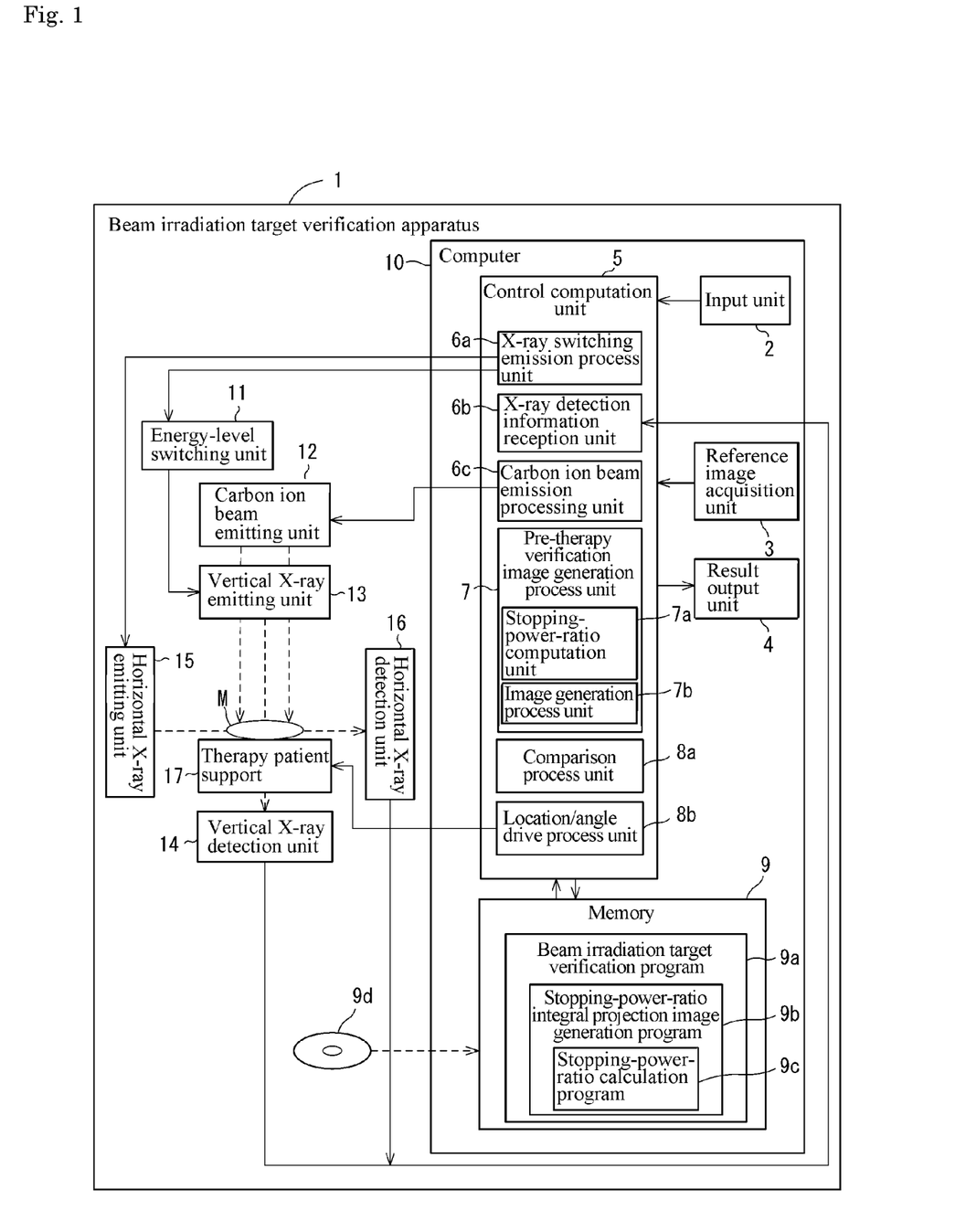
FIG. 1 is a block diagram illustrating a configuration of a beam irradiation target verification apparatus for therapy.

FIG. 1 is a block diagram illustrating a configuration of a beam irradiation target verification apparatus 1. The beam irradiation target verification apparatus 1 includes a computer 10, an energy-level switching unit 11, a carbon ion beam emitting unit 12, a vertical X-ray emitting unit 13 (X-ray emitting unit), a vertical X-ray detection unit 14 (X-ray detection unit), a horizontal X-ray emitting unit 15, a horizontal X-ray detection unit 16, and a therapy patient support 17.

The computer 10 includes an input unit 2, a reference image acquisition unit 3, a result output unit 4, a control computation unit 5, and a memory 9. The control computation unit 5 includes an X-ray switching emission process unit 6a, an X-ray detection information reception unit 6b, a carbon ion beam emission process unit 6c, a pre-therapy verification image generation process unit 7, a comparison process unit 8a, and a location/angle drive process unit 8b.

The input unit 2 receives an input for operation by medical personnel, including a medical doctor, at a distant location from a therapy patient M. The input unit 2 includes, for example, a keyboard and a mouse, or a touch panel. This input unit 2 receives an input of operation information on an operation of the energy-level switching unit 11 and/or the therapy patient support 17.

The reference image acquisition unit 3 includes an I/O interface, such as a USB port, a serial port, or a LAN port, and acquires a previously generated reference image from an external device, such as another computer or a USB memory. The reference image is a two-dimensional image of stopping power ratios calculated based on a CT image captured at the therapy planning stage. As used herein, the term "stopping power ratio" represents an effective thickness of the patient in terms of a particle beam. The reference image is not limited to the two-dimensional image of the calculated stopping power ratios, but may also be the CT image itself.

The result output unit 4 outputs a result of computation performed by the control computation unit 5. The result output unit 4 includes a display device, such as, for example, a cathode ray tube (CRT) or a liquid crystal display. The result output unit 4 may display a reference image, a two-dimensional image, a determination result and the like.

The control computation unit 5 performs various control operations and computations according to various programs, such as a beam irradiation target verification program 9a, a stopping-power-ratio integral projection image generation program 9b, and a stopping-power-ratio calculation program 9c, each stored in the memory 9.

The X-ray switching emission process unit 6a controls the energy-level switching unit 11. This control is provided such that the X-ray switching emission process unit 6a causes the voltage supplied to the vertical X-ray emitting unit 13 to be switched to a first level of energy, waits until the X-ray emission by the vertical X-ray emitting unit 13 completes, and after the completion, causes the voltage to be switched to a second level of energy. Thus, the X-ray switching emission process unit 6a performs a switching operation of the level of the energy supplied to the vertical X-ray emitting unit 13 between various levels, and maintains the level of energy at a constant level during the emission of an X-ray by the vertical X-ray emitting unit 13.

The X-ray detection information reception unit 6b obtains detection information of the X-rays detected by the vertical X-ray detection unit 14 and by the horizontal X-ray detection unit 16.

The carbon ion beam emission process unit 6c controls and causes the carbon ion beam emitting unit 12 to emit a desired carbon ion beam to the therapy patient M.

The pre-therapy verification image generation process unit 7 includes a stopping-power-ratio computation unit 7a and an image generation process unit 7b.

The stopping-power-ratio computation unit 7a performs a process of computing a stopping power ratio from an X-ray image set captured using two levels of X-ray energy that have been obtained in the vertical X-ray detection unit 14. Hereinafter, a process of computationally generating a two-dimensional image of stopping power ratio from an X-ray image set captured using two levels of X-ray energy will be described.

First, a first two-dimensional X-ray image captured by emitting an X-ray having a first energy level $E_1$, and a second two-dimensional X-ray image captured by emitting an X-ray having a second energy level $E_2$ from the same location from the same direction are obtained. A pixel value in each two-dimensional X-ray image obtained in this manner represents a degree of X-ray attenuation (source attenuation coefficient μ) along a linear path from the source to the detection location.

In this regard, a source attenuation coefficient μ of an X-ray depends primarily on an electron density $ρ_e$ and an effective atomic number Z of the therapy patient M (irradiation object). That is, a source attenuation coefficient μ can be obtained from an equation containing the electron density $ρ_e$ and the effective atomic number Z as parameters.

Among the three parameters μ, $ρ_e$, and Z, the source attenuation coefficient μ can be determined by a pixel value of the two-dimensional X-ray image. Thus, the degrees of attenuation ($μ_1$, $μ_2$) of the X-rays having the two levels of energy ($E_1$, $E_2$) can be determined. Solving an equation containing $μ_1$, $ρ_e$, and Z, and an equation containing $μ_2$, $ρ_e$, and Z as a set of simultaneous equations can determine the electron density $ρ_e$ and the effective atomic number Z of the therapy patient M along the linear path in the therapy patient M.

Note that an effective atomic number Z of a substance and its mean excitation energy I exhibit a highly linear correlation, such as one shown by an equation: I=aZ+b. Values of "a" and "b" in this equation are each uniquely determined regardless of the level of energy of X-ray. Along with the correlativity described above, this fact has been found by Yang et al. (*1).

*1 M. Yang and five others, "Theoretical variance analysis of single- and dual-energy computed tomography methods for calculating proton stopping power ratios of biological tissues," Physics in Medicine and Biology (UK), IOP Publishing, Feb. 10, 2010, vol. 55, no. 5, pp. 1343-1362.

By using this relationship, the value of I of that substance can be determined from the effective atomic number Z obtained from two images.

A stopping power ratio, to water, of a substance in the body that determines the stopping location of a particle beam in the body can be calculated using Equation 1 presented below.

$$\frac{S}{S_{water}} \approx \frac{\rho_e}{\rho_{e,water}} \cdot \frac{\ln\left(\frac{2m_e c^2}{I}\right) - 0.5}{\ln\left(\frac{2m_e c^2}{I_{water}}\right) - 0.5}$$ [Equation 1]

where S represents a stopping power, ρ represents an electron density, I represents mean excitation energy, $m_e c^2$ represents rest energy of an electron, and ln represents logarithm; and $S_{water}$, $\rho_e$, water, and $I_{water}$ respectively represent a stopping power, an electron density, and mean excitation energy of water, and are given as constants.

The image generation process unit 7b performs a process of generating a pre-therapy verification image (two-dimensional image). The value of each pixel (pixel value) in the pre-therapy verification image (two-dimensional image) is a stopping power ratio (S/$S_{water}$) of the pixel computed by the stopping-power-ratio computation unit 7a. Thus, a two-dimensional image generated by integrally projecting the stopping power ratios (stopping-power-ratio integral projection image) of the therapy patient M along the beam axis direction is obtained. In other words, a pre-therapy verification image can be directly obtained from a first two-dimensional X-ray image and a second two-dimensional X-ray image based on two types of X-ray energy having different levels of energy, via an image in association with $\rho_e$ and I.

The comparison process unit 8a compares the pre-therapy verification image obtained by the pre-therapy verification image generation process unit 7 and the reference image obtained by the reference image acquisition unit 3, and outputs a comparison result to the result output unit 4. The content of the output has an appropriate structure, such as, for example, a window displaying the reference image and the pre-therapy verification image in a comparable manner; a window displaying, with numerical values or ranking, a result of density comparison between each pair of pixels in the reference image and in the pre-therapy verification image; a window displaying an adequacy determination result determined from the comparison result in terms of adequacy; or a combination thereof. The determination of adequacy may be based on an appropriate criterion, such as a degree of difference in the density, or the area of a region having differences in the density.

The location/angle drive process unit 8b drives and controls the therapy patient support 17 to adjust the location and angle thereof so that the relative location of the therapy patient M with respect to the carbon ion beam emitting unit 12 will be appropriate for the therapy plan. In more detail, particle beam therapy is performed in such a way that, in the therapy room, the patient is "positioned" at a location presumed in the therapy plan, and is then irradiated for therapy. This "positioning" is performed in such a way that X-ray imaging is performed using the vertical X-ray emitting unit 13 facing a direction of the beam irradiation of the particle beam (carbon ion beam) and the horizontal X-ray emitting unit 15 facing a direction perpendicular to that direction, and the therapy patient support 17 or the therapy patient, directly, is moved while it is monitored whether the therapy patient on the therapy patient support 17 is fixedly held at the location presumed in the therapy plan, or otherwise is lying out of position. That is, such adjustment by movement may either be manual adjustment based on an operational input on the input unit 2, or automatic adjustment provided by the location/angle drive process unit 8b.

The memory 9 stores various programs, such as the beam irradiation target verification program 9a, the stopping-power-ratio integral projection image generation program 9b, and the stopping-power-ratio calculation program 9c, as well as various data. These programs and data are installed or copied from a recording medium 9d, such as a CR-ROM or a DVD-ROM, and are stored in the memory 9.

The energy-level switching unit 11 switches the energy level of an X-ray emitted from the vertical X-ray emitting unit 13 to an appropriate energy level, such as the first energy level $E_1$ or the second energy level $E_2$, under the control of the X-ray switching emission process unit 6a. The first energy level $E_1$ corresponds to a tube voltage of the X-ray source, which is set preferably to 80 kV or higher, and more preferably to 100 kV or higher. A difference between the first energy level $E_1$ and the second energy level $E_2$ (tube voltage difference) may be 50 kV or higher, more preferably 100 kV or higher, and still more preferably 900 kV or higher.

In this embodiment, the first energy level $E_1$ is assumed to be 100 kV, which is its preferred level of energy; and the second energy level $E_2$ is assumed to be 1 MV, which is its preferred level of energy (i.e., a level of energy corresponding to a preferred energy difference of 900 kV). These energy levels ($E_1$, $E_2$) may be set appropriately, for example, may be set in advance, or set by an input at the input unit 2.

The carbon ion beam emitting unit 12 emits an accelerated carbon ion beam to the therapy patient M under the control of the control computation unit 5. In more detail, the carbon ion beam emitting unit 12 is provided with a charged particle generator, an accelerator, and a beam emitting unit. The charged particle generator includes an ion source for generating a desired ion species, and the like. This embodiment assumes that the ion source generates carbon ions. The accelerator is a device such as a synchrotron that accelerates the charged particles (in this embodiment, carbon ions) received from the charged particle generator. The accelerator then transmits the accelerated charged particles to the beam emitting unit. The beam emitting unit adjusts the beam shape of the carbon ion beam to a desired shape by a collimator or the like, and then emits a carbon ion beam to the therapy patient M. The carbon ion beam emitting unit 12 configured as described above emits a carbon ion beam having a planned energy level and a planned shape according to the therapy plan. The carbon ion beam emitted by the carbon ion beam emitting unit 12 may alternatively be a proton beam or other particle beam for use in particle beam therapy.

The vertical X-ray emitting unit (first X-ray emitting unit) 13 emits an X-ray having an energy level, to which the energy-level switching unit 11 has switched, to the therapy patient M in a vertical direction under the control of the control computation unit 5. The number of types of the X-rays emitted by the vertical X-ray emitting unit 13 is at least two: a first X-ray emitted with the first energy level $E_1$; and a second X-ray emitted with the second energy level $E_2$.

The vertical X-ray detection unit (first X-ray detection unit) 14 detects an X-ray emitted by the vertical X-ray emitting unit 13, and transmits the detection information thereof to the control computation unit 5.

The horizontal X-ray emitting unit (second X-ray emitting unit) 15 emits an X-ray to the therapy patient M in a direction parallel to the therapy patient support 17 under the control of the control computation unit 5.

The horizontal X-ray detection unit (second X-ray detection unit) 16 detects an X-ray emitted by the horizontal X-ray emitting unit 15, and transmits the detection information thereof to the control computation unit 5.

The X-rays emitted from the vertical X-ray emitting unit 13 and the horizontal X-ray emitting unit 15 are emitted from different directions for positioning. Thus, these X-rays preferably cross orthogonally to each other. These directions are not limited to 0° (horizontal) and 90° (vertical) as in this embodiment, but may also be an appropriate pair of angles, such as 45° and 135°.

The therapy patient support 17 supports the body of the therapy patient M lying on the table thereof, and performs positioning of the therapy patient M. The therapy patient support 17 includes an appropriate drive unit to change the tilt, location, and the like under the control of the control computation unit 5. Note that the therapy patient support 17 needs only to have capability to fix the location of a target organ of the therapy patient M, and the table thereof may thus be non-horizontal.

Figure 2:
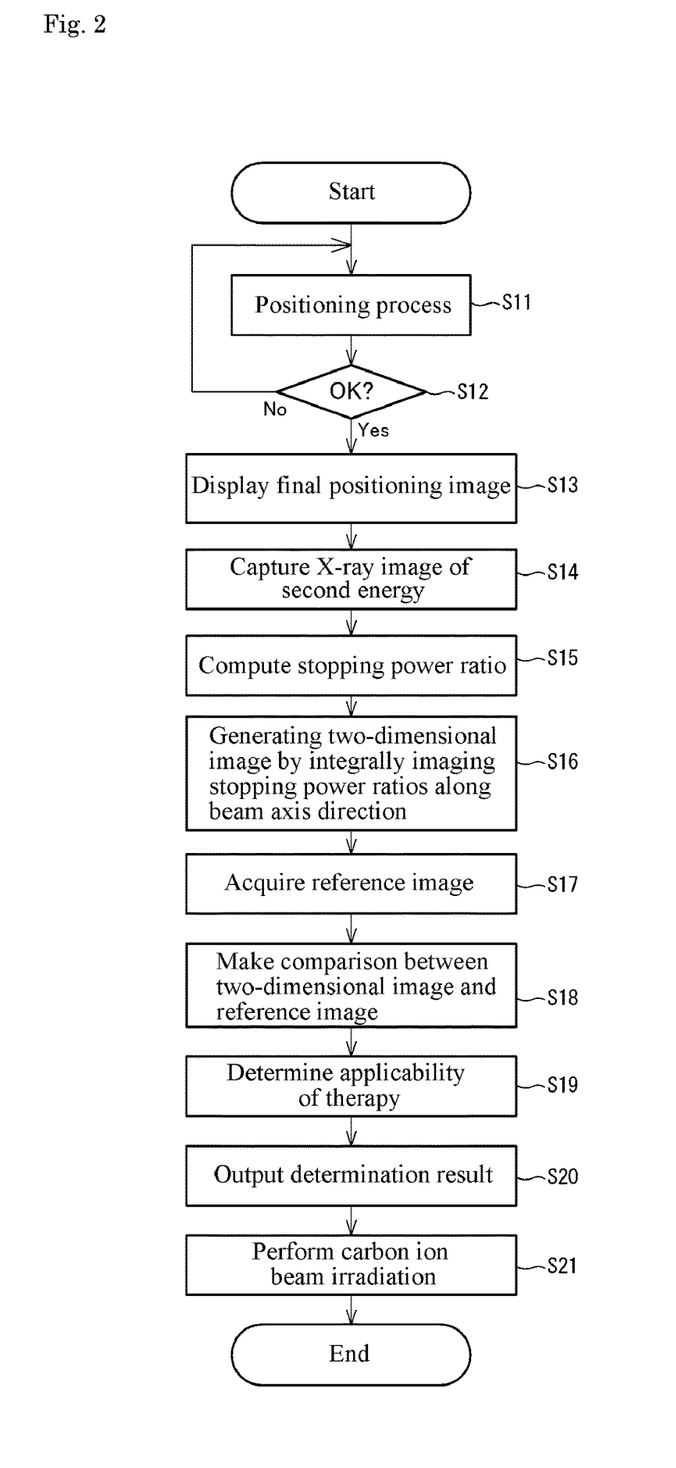
FIG. 2 is a flowchart illustrating an operation of the beam irradiation target verification apparatus for therapy.

FIG. 2 is a flowchart illustrating an operation performed by the control computation unit 5 of the beam irradiation target verification apparatus 1 according to the beam irradiation target verification program 9a, the stopping-power-ratio integral projection image generation program 9b, and the stopping-power-ratio calculation program 9c.

The control computation unit 5 executes the beam irradiation target verification program 9a to perform a positioning process (step S11). In this positioning process, the control computation unit 5 performs x-ray emission from the vertical X-ray emitting unit 13 and the horizontal X-ray emitting unit 15 via a control process of the X-ray switching emission process unit 6a, allows the X-rays to be detected by the vertical X-ray detection unit 14 and the horizontal X-ray detection unit 16, and then receives the detection information at the X-ray detection information reception unit 6b. Then, the control computation unit 5 changes the location and angle of the therapy patient support 17 based on the detection information to match the relative location of the therapy patient M with respect to the carbon ion beam emitting unit 12 to the relative location determined at the time of therapy planning. This positioning process is performed in such a manner that, among the pieces of the detection information detected by the vertical X-ray detection unit 14 and the horizontal X-ray detection unit 16, the location of a bone etc. of the therapy patient M, for example, is checked to ensure the location to match the location as has been planned. In this positioning process, the control computation unit 5 controls the energy-level switching unit 11 so that the energy level of the X-ray emitted by the vertical X-ray emitting unit 13 will be the first energy level $E_1$. This enables the X-ray image for positioning to be provided as an X-ray image associated with a first energy.

After changing the location and angle in the positioning process, the control computation unit 5 obtains again the detection information based on X-rays in the two directions, and checks whether the relative location of the therapy patient M with respect to the carbon ion beam emitting unit 12 matches the location as has been planned (step S12). If it is determined that no match is found, the control computation unit 5 repeats the positioning process (step S12: No).

After completion of the positioning process (step S12: Yes), the control computation unit 5 displays a final positioning image on the result output unit 4 (step S13). The final positioning image is an X-ray image obtained for the last time by the vertical X-ray detection unit 14 and the horizontal X-ray detection unit 16 after completion of positioning, and is displayed for a verification purpose.

The control computation unit 5 uses the X-ray switching emission process unit 6a to control the energy-level switching unit 11 to switch the level of energy of the X-ray emitted by the vertical X-ray emitting unit 13 to a second energy level $E_2$ different from the level of energy of the X-ray used in the positioning process. The control computation unit 5 then captures an X-ray image associated with a second energy using the vertical X-ray emitting unit 13 and the vertical X-ray detection unit 14; and obtains the detection information using the X-ray detection information reception unit 6b (step S14).

The control computation unit 5 performs a process of computing the stopping power ratio of each pixel of a two-dimensional image based on the dual-energy X-ray image set using the stopping-power-ratio computation unit 7a of the pre-therapy verification image generation process unit 7, according to the stopping-power-ratio calculation program 9c (step S15).

The control computation unit 5 performs a process of generating a two-dimensional image by integrally imaging the stopping power ratios calculated based on the dual-energy X-ray image set along the beam axis direction using the image generation process unit 7b of the pre-therapy verification image generation process unit 7, according to the stopping-power-ratio integral projection image generation program 9b (step S16).

That is, the control computation unit 5 performs at steps S11 and S14 a process of X-ray imaging using two levels of X-ray energy from the beam emission direction, and obtains a two-dimensional X-ray image set corresponding to these energy levels; and thus computes the stopping power ratio of each pair of pixels of the two-dimensional X-ray image set to computationally generate a two-dimensional image of stopping power ratios.

The control computation unit 5 uses the reference image acquisition unit 3 to acquire a reference image obtained at the therapy planning stage (step S17).

The control computation unit 5 uses the comparison process unit 8a to make a comparison between the reference image acquired at step S17 and the two-dimensional image of stopping power ratios generated at step 15 (step S18).

The control computation unit 5 uses the comparison process unit 8a to determine applicability of therapy based on the comparison result of step S18 (step S19).

The control computation unit 5 outputs the comparison result of step S18 and the determination result of step S19 to the result output unit 4 (step S20).

The control computation unit 5 uses the carbon ion beam emission process unit 6c to drive and control the carbon ion beam emitting unit 12 to perform carbon ion beam irradiation when the determination result indicates that therapy is applicable and when an instruction to perform particle beam therapy (carbon ion beam therapy) is received (step S21).

Figure 3:
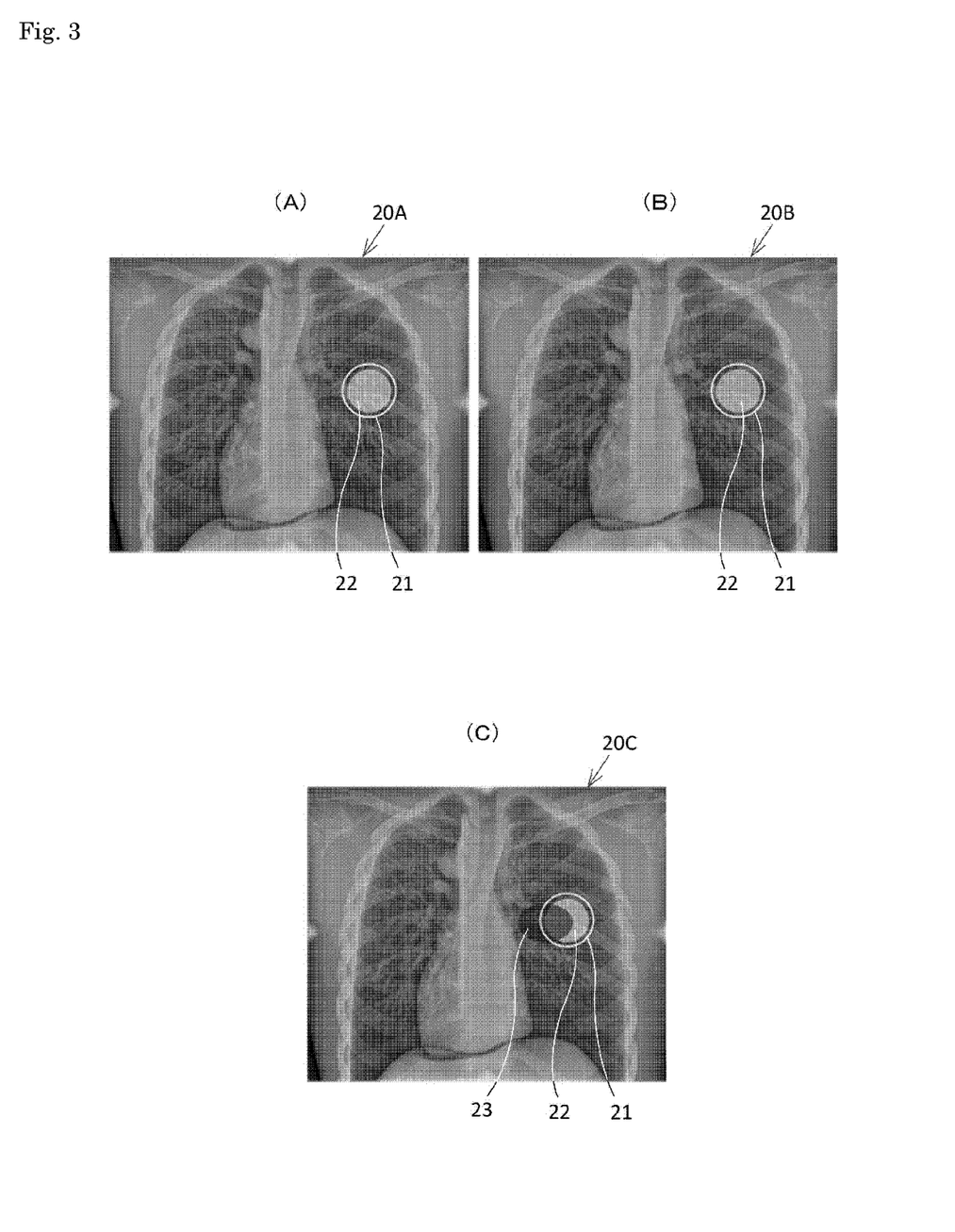
FIG. 3 is a set of illustrative images for comparisons between a therapy planning image and pre-therapy verification images.

FIG. 3 is a set of illustrative images for comparisons between a reference image 20A using an image at the time of therapy planning and pretherapy verification images 20B and 20C based on image capturing prior to a therapy.

FIG. 3(A) shows a previously generated reference image 20A acquired by the reference image acquisition unit 3. The reference image 20A is a two-dimensional image of stopping power ratios calculated based on a CT image captured at the therapy planning stage. In the therapy planning, a therapy target region 21 has been defined for a tumor 22 as illustrated. The therapy target region 21 has a size similar to, or slightly greater than, the tumor 22.

FIG. 3(B) shows a pre-therapy verification image 20B, which is a two-dimensional image of stopping power ratios (stopping-power-ratio integral projection image) generated by the pre-therapy verification image generation process unit 7 based on an image set in association with two levels of X-ray energy. The pre-therapy verification image 20B shown in FIG. 3(B) is characterized in that the difference of an effective thickness down to the therapy target region 21 estimated from a value of integral of stopping power ratios inside and near the therapy target region 21, from that of the reference image 20A at the time of therapy planning, is at or below an acceptable limit. Accordingly, the comparison process unit 8a determines that the pre-therapy verification image 20B indicates that therapy is applicable to the therapy patient. This acceptable limit is a threshold, and is preferably, for example, about 2 mm.

Similarly to FIG. 3(B), FIG. 3(C) shows a pre-therapy verification image 20C, which is another two-dimensional image of stopping power ratios (stopping-power-ratio integral projection image) generated based on an image set in association with two levels of X-ray energy prior to the therapy irradiation. This pre-therapy verification image 20C is a two-dimensional image of stopping power ratios of a therapy patient M having a low density material 23, such as air, introduced on the X-ray path before the therapy target region 21.

The pre-therapy verification image 20C shown in FIG. 3(C) is characterized in that the difference of an effective thickness down to the therapy target region 21 estimated from a value of integral of stopping power ratios inside and near the therapy target region 21 exceeds an acceptable limit, compared to that of the reference image 20A at the time of therapy planning. Accordingly, the comparison process unit 8a determines that the pre-therapy verification image 20C indicates that therapy is not applicable to the therapy patient. This acceptable limit is a threshold, and is preferably, for example, about 2 mm.

If it is determined that therapy is not applicable as described above, CT imaging is repeated and a therapy plan is made again. This making process of a new therapy plan can be performed at any stage during a therapy including multiple applications of carbon ion beam irradiation according to the initial therapy plan. Thus, the therapy plan can be reworked at any time when the therapy is found to be no more applicable due to a change in location, size, etc. of the tumor differing from what has been presumed upon therapy planning. Thus, a flexible and appropriate therapy can be performed depending on the situation.

The configuration and operation described above enables the beam irradiation target verification apparatus 1 to measure internal conditions of a therapy patient, and to determine necessity of changing the therapy plan, easily and at a relatively low exposure level. Accordingly, when the location etc. of the tumor has changed from that of the therapy plan, flexible and appropriate measures can be taken depending on the progress of therapy, including making a therapy plan again and changing irradiation parameters. The beam range inside the body and a change thereof from that of the therapy plan can also be estimated prior to therapy irradiation. Furthermore, exposure of normal tissue other than the tumor can be minimized.

The beam irradiation target verification apparatus 1 is capable of calculating a stopping power ratio viewed from the direction of the carbon ion beam irradiation using only one vertical X-ray emitting unit 13 that emits an X-ray from the same direction. This enables the beam irradiation target verification apparatus 1 to determine, with high accuracy, adequacy of performing carbon ion beam irradiation according to the therapy plan prior to the therapy. In particular, unlike a method of verification using CT imaging prior to a therapy, there is no need for the therapy patient to move between verification and therapy, and thus the beam irradiation target verification apparatus 1 can determine the adequacy using an accurate location.

As for the amount of exposure, the beam irradiation target verification apparatus 1 requires only one more irradiation operation of second X-ray irradiation in addition to the X-ray irradiation performed during positioning as compared with conventional carbon ion beam therapy. Thus, the beam irradiation target verification apparatus 1 enables the amount of exposure of the therapy patient to be significantly reduced as compared with a method using CT imaging prior to a therapy.

Moreover, as compared with a method of detecting a carbon ion beam passed through the therapy patient using carbon ion beam radiography, the beam irradiation target verification apparatus 1 requires no large-scale accelerator facility, and is thus usable in a typical particle beam therapy facility.

The beam irradiation target verification program 9a incorporating the stopping-power-ratio integral projection image generation program 9b and the stopping-power-ratio calculation program 9c enables the present invention to be practiced only by installing the program in a carbon ion beam irradiation apparatus having an X-ray emitting unit for positioning or other purpose. Thus, the present invention can be embodied in an existing apparatus easily and at low cost.

The use of the first energy level $E_1$ of 80 kV or higher can eliminate effects of hardening of the X-ray.

In addition, setting the difference between the first energy levels $E_1$ and the second energy level $E_2$ to a predetermined value or higher (e.g., 50 kV or higher) enables stopping power ratios to be appropriately calculated.

Comparisons between the reference image 20A obtained at the therapy planning stage and the pre-therapy verification images 20B and 20C obtained prior to therapy irradiation by dual-energy X-ray imaging enable the beam range inside the body in that irradiation and a change thereof from that of the therapy plan to be estimated. Such information may provide an opportunity for determining applicability of that therapy irradiation, recapturing a CT image for therapy planning, and redesigning the therapy plan.

Furthermore, the beam irradiation target verification apparatus 1 can provide an accumulation of data of changes in beam range inside the body in routine therapy, which has not heretofore existed. This allows valuable data to be provided for development in particle beam therapy.

Note that the reference image 20A may be a reference image that is a two-dimensional image of stopping power ratios obtained by performing dual-energy simple X-ray photography similar to one provided by the present invention upon capturing a CT image for the therapy plan. The reference image 20A is not limited to an image based on a CT image, but may also be computationally generated by other method.

The control computation unit 5 may be configured to obtain a CT image itself using the reference image acquisition unit 3, and to perform a computational operation of computationally generating, from this CT image, a two-dimensional image of stopping power ratios viewed in the beam axis direction.

The carbon ion beam emitting unit 12 may be configured to emit a carbon ion beam not only in the vertical direction, but also in an appropriate direction, such as in a horizontal direction, or in an arbitrary direction by using a gantry. In such case, the vertical X-ray emitting unit 13 connected to the energy-level switching unit 11 may be configured to emit an X-ray from the same direction as the carbon ion beam emitting unit 12. For example, if the carbon ion beam emitting unit 12 is configured to emit a carbon ion beam in a horizontal direction, then the energy-level switching unit 11 may be arranged to be connected to the horizontal X-ray emitting unit 15 (X-ray emitting unit). Then, the energy level of the X-ray emitted from the horizontal X-ray emitting unit 15 can be switched using the energy-level switching unit 11 to obtain a dual-energy X-ray image set, from which a two-dimensional image is generated by integrally imaging the stopping power ratios in the beam axis direction. Such configuration can also provide the same functions and advantages as those provided by the embodiment described above.

INDUSTRIAL APPLICABILITY

The present invention is applicable to particle beam therapy and in various fields requiring a stopping power ratio.

REFERENCE SIGNS LIST

1: Beam irradiation target verification apparatus
3: Reference image acquisition unit
4: Result output unit
6a: X-ray switching emission process unit
6b: X-ray detection information reception unit
7: Pre-therapy verification image generation process unit
7a: Stopping-power-ratio computation unit
8a: Comparison process unit
9a: Beam irradiation target verification program
9c: Stopping-power-ratio calculation program
10: Computer
11: Energy-level switching unit
13: Vertical X-ray emitting unit
14: Vertical X-ray detection unit
20A: Reference image
20B, 20C: Pre-therapy verification image
FIG. 1
(1) Beam irradiation target verification apparatus
(2) Input unit
(3) Reference image acquisition unit
(4) Result output unit
(5) Control computation unit
(6a) X-ray switching emission process unit
(6b) X-ray detection information reception unit
(6c) Carbon ion beam emission processing unit
(7) Pre-therapy verification image generation process unit
(7a) Stopping-power-ratio computation unit
(7b) Image generation process unit
(8a) Comparison process unit
(8b) Location/angle drive process unit
(9) Memory
(9a) Beam irradiation target verification program
(9b) Stopping-power-ratio integral projection image generation program
(9c) Stopping-power-ratio calculation program
(10) Computer
(11) Energy-level switching unit
(12) Carbon ion beam emitting unit
(13) Vertical X-ray emitting unit
(14) Vertical X-ray detection unit
(15) Horizontal X-ray emitting unit
(16) Horizontal X-ray detection unit
(17) Therapy patient support
FIG. 2
(1) Start
(S11) Positioning process
(S13) Display final positioning image
(S14) Capture X-ray image of second energy
(S15) Compute stopping power ratio
(S16) Generating two-dimensional image by integrally imaging stopping power ratios along beam axis direction
(S17) Acquire reference image
(S18) Make comparison between two-dimensional image and reference image
(S19) Determine applicability of therapy
(S20) Output determination result
(S21) Perform carbon ion beam irradiation
(2) End

The invention claimed is:

1. A beam irradiation target verification apparatus comprising:
an X-ray emitting unit configured to emit an X-ray;
an energy-level switching unit configured to switch an energy level of the X-ray to be emitted by the X-ray emitting unit;
an X-ray switching emission process unit configured to cause the energy-level switching unit to switch the energy level of the X-ray to be emitted by the X-ray emitting unit from a first energy level to a second energy level different from the first energy level, and to cause the X-ray unit to emit an X-ray at the second energy level;
an X-ray detection unit configured to detect the X-ray emitted from the X-ray emitting unit at the first energy level and the X-ray emitted from the X-ray emitting unit at the second energy level;
a location/angle drive process unit configured to match a relative location of a therapy patient to a relative location determined at a time of therapy planning based on first detection information, detected by the X-ray detection unit, of the X-ray emitted by the X-ray emitting unit at the first energy level, wherein the switch of the energy level of the X-ray to be emitted by the X-ray emitting unit is after the relative locations are matched;
a pre-therapy verification image generation process unit configured to generate a pre-therapy verification image based on the first detection information and second detection information, wherein the second detection information is detected by the X-ray detection unit after matching the relative locations;
a reference image acquisition unit configured to acquire a reference image obtained at a therapy planning stage;
a comparison process unit configured to make a comparison between the pre-therapy verification image and the reference image; and
a result output unit configured to output a comparison result obtained by the comparison process unit.

2. The beam irradiation target verification apparatus according to claim 1, wherein the reference image acquired by the reference image acquisition unit is a reference image of stopping power ratios calculated at the therapy planning stage, and the pre-therapy verification image generated in the recent pre-therapy image generation process unit is a pre-therapy verification image of stopping power ratios calculated based on the first detection information and the second detection information.

3. The beam irradiation target verification apparatus according to claim 2, wherein the pre-therapy verification image generation process unit is configured to:
  calculate source attenuation coefficients obtainable based on the first detection information and the second detection information, and
  obtain an electron density and an effective atomic number by substituting the source attenuation coefficients of the X-ray at the first energy level and the X-ray at the second energy level into an equation having an electron density, an effective atomic number, and a source attenuation coefficient, and by solving a set of simultaneous equations yielded, and calculate stopping power ratios based on the electron density and the effective atomic number.

4. The beam irradiation target verification apparatus according to claim 2, wherein the location/angle drive process unit is configured to match the relative location of the therapy patient to the relative location determined at the time of therapy planning by at least:
  changing a location and an angle of the therapy patient based on detection, by the X-ray detection unit, of the X-ray emitted by the X-ray emitting unit at the first energy level,
  verifying whether the location and the angle of the therapy patient after the changing matches a location and an angle determined at the time of therapy planning based on detection of the X-ray with the first energy level being re-emitted by the X-ray emitting unit, and
  when the location and the angle after the change does not match the location and the angle determined at the time of therapy planning, repeating the changing and the verifying until the relative location of the therapy patient matches the relative location determined at the time of therapy planning, and
the pre-therapy verification image generation process unit is configured to generate the pre-therapy verification image that is a pre-therapy verification image of stopping power ratios calculated based on the first detection information and the second detection information, wherein the first detection information is on the detection of the verifying in which the location and the angle of the therapy patient matches the location and the angle determined at the time of therapy planning.

5. The beam irradiation target verification apparatus according to claim 2, wherein the X-ray emitting unit is configured to emit the X-rays at the first energy level and at the second energy level in a same direction as a direction of a beam is emitted by the X-ray emitting unit, and the first detection information and the second detection information are information on detection of the X-rays emitted in a same direction as a direction in which the beam is emitted by the X-ray emitting unit.

6. A non-transitory storage medium comprising:

a beam irradiation target verification program stored on the non-transitory storage medium for causing a computer to function as:

an X-ray detection information reception unit configured to receive first detection information, detected by an X-ray detection unit, of an X-ray emitted from an X-ray emitting unit at a first energy level, and to receive second detection information, detected by the X-ray detection unit, of an X-ray emitted from the X-ray emitting unit at a second energy level different from the first energy level;

a location/angle drive process unit configured to match a relative location of a therapy patient to a relative location determined at a time of therapy planning based on the first detection information;

an X-ray switching emission process unit configured to, after the relative locations are matched, cause an energy-level switching unit to switch an energy level of an X-ray to be emitted by the X-ray emitting unit from the first energy level to the second energy level, and to cause the X-ray emitting unit to emit the X-ray at the second energy level;

a pre-therapy verification image generation process unit configured to generate a pre-therapy verification image based on the first detection information and the second detection information, wherein the second detection information, is detected by the X-ray detection unit after matching the relative locations;

a reference image acquisition unit configured to acquire a reference image at a therapy planning stage;

a comparison process unit configured to make a comparison between the pre-therapy verification image and the reference image; and a result output unit configured to output a comparison result obtained by the comparison process unit.

* * * * *